US006730072B2

(12) United States Patent
Shawgo et al.

(10) Patent No.: US 6,730,072 B2
(45) Date of Patent: May 4, 2004

(54) METHODS AND DEVICES FOR SEALING MICROCHIP RESERVOIR DEVICES

(75) Inventors: Rebecca S. Shawgo, Cambridge, MA (US); Norman F. Sheppard, Jr., Bedford, MA (US); Michael J. Cima, Winchester, MA (US); John T. Santini, Jr., Belmont, MA (US); Stephen J. Herman, Andover, MA (US); Benjamin F. Polito, Cambridge, MA (US); Scott A. Uhland, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 175 days.

(21) Appl. No.: 09/867,976

(22) Filed: May 30, 2001

(65) Prior Publication Data

US 2002/0151776 A1 Oct. 17, 2002

Related U.S. Application Data

(60) Provisional application No. 60/207,814, filed on May 30, 2000.

(51) Int. Cl.[7] .................................................. A61K 9/22
(52) U.S. Cl. ..................................... 604/890.1; 128/898
(58) Field of Search ......................... 604/890.1, 891.1, 604/93.01, 20, 131; 128/898

(56) References Cited

U.S. PATENT DOCUMENTS

| | | |
|---|---|---|
| 3,692,027 A | 9/1972 | Ellinwood, Jr. |
| 4,003,379 A | 1/1977 | Ellinwood, Jr. |
| 4,360,019 A | 11/1982 | Portner et al. |
| 4,507,115 A | 3/1985 | Kambara et al. |
| 4,585,652 A | 4/1986 | Miller et al. |
| 4,731,049 A | 3/1988 | Parsi |
| 4,793,825 A | 12/1988 | Benjamin et al. |
| 5,042,975 A | 8/1991 | Chien et al. |
| 5,167,625 A | 12/1992 | Jacobsen et al. |

(List continued on next page.)

FOREIGN PATENT DOCUMENTS

| | | |
|---|---|---|
| WO | 93/03790 | 3/1993 |
| WO | 98/26814 | 6/1998 |
| WO | 99/09960 | 3/1999 |
| WO | 99/52590 | 10/1999 |

OTHER PUBLICATIONS

Bhattacharya & Tummala, "Next Generation Integral Passives: Materials, Processes, and Integration of Resistors and Capacitors on PWB Substrates," *J. Mater. Sci.–Mater. Electron.* 11(3):253–68 (2000).

(List continued on next page.)

*Primary Examiner*—Manuel Mendez
*Assistant Examiner*—Michael M Thompson
(74) *Attorney, Agent, or Firm*—Sutherland Asbill & Brennan LLP (57) ABSTRACT

Methods and devices are provided for mechanically sealing the reservoirs of microchip devices to prevent leakage from or between any of the reservoirs. In one embodiment, the method includes sandwiching a microchip device and a gasket material covering the reservoir openings between a front sealing frame and a backplate, such that the gasket material is compressed against the back side of the microchip device by the back plate. The front sealing frame is secured to the back sealing plate using fasteners or welding. The gasket material is preferably a flexible polymeric sheet, which is biocompatible and compatible with the reservoir contents. In another embodiment, a composite backplate is used in place of the back sealing plate and separate gasket material. The composite backplate can include a substrate having sealing plugs defined thereon. The composite backplate also can be designed to hold the drug, thereby combining the assembly steps of reservoir filling and sealing.

25 Claims, 9 Drawing Sheets

U.S. PATENT DOCUMENTS

| | | |
|---|---|---|
| 5,170,801 A | 12/1992 | Casper et al. |
| 5,196,002 A | 3/1993 | Hanover et al. |
| 5,200,051 A | 4/1993 | Cozzette et al. |
| 5,252,294 A | 10/1993 | Kroy et al. |
| 5,279,607 A | 1/1994 | Schentag et al. |
| 5,304,293 A | 4/1994 | Tierney et al. |
| 5,318,557 A | 6/1994 | Gross |
| 5,336,213 A | 8/1994 | D'Angelo et al. |
| 5,344,454 A | 9/1994 | Clarke et al. |
| 5,366,454 A | 11/1994 | Currie et al. |
| 5,368,588 A | 11/1994 | Bettinger et al. |
| 5,368,704 A | 11/1994 | Madou et al. |
| 5,427,585 A | 6/1995 | Bettinger |
| 5,443,508 A | 8/1995 | Giampapa |
| 5,474,527 A | 12/1995 | Bettinger |
| 5,490,962 A | 2/1996 | Cima et al. |
| 5,516,490 A | 5/1996 | Sanadi |
| 5,585,069 A | 12/1996 | Zanzucchi et al. |
| 5,651,900 A | 7/1997 | Keller et al. |
| 5,660,680 A | 8/1997 | Keller |
| 5,770,076 A | 6/1998 | Chu et al. |
| 5,792,048 A | 8/1998 | Schaefer |
| 5,797,898 A | 8/1998 | Santini, Jr. et al. |
| 5,798,042 A | 8/1998 | Chu et al. |
| 5,824,204 A | 10/1998 | Jerman |
| 5,842,787 A | 12/1998 | Kopf-Sill et al. |
| 5,843,767 A | 12/1998 | Beattie |
| 5,858,770 A | 1/1999 | Perlman |
| 5,869,004 A | 2/1999 | Parce et al. |
| 5,872,010 A | 2/1999 | Karger et al. |
| 5,893,974 A | 4/1999 | Keller et al. |
| 5,900,160 A | 5/1999 | Whitesides et al. |
| 5,938,923 A | 8/1999 | Tu et al. |
| 5,948,255 A | 9/1999 | Keller et al. |
| 5,962,081 A | 10/1999 | Öhman et al. |
| 5,976,336 A | 11/1999 | Dubrow et al. |
| 5,989,445 A | 11/1999 | Wise et al. |
| 6,027,695 A | 2/2000 | Oldenburg et al. |
| 6,042,710 A | 3/2000 | Dubrow |
| 6,068,752 A | 5/2000 | Dubrow et al. |
| 6,083,763 A | 7/2000 | Balch |
| 6,096,656 A | 8/2000 | Matzke et al. |
| 6,114,658 A | 9/2000 | Roth et al. |
| 6,123,861 A | 9/2000 | Santini, Jr. et al. |
| 6,136,212 A | 10/2000 | Mastrangelo et al. |
| 6,171,850 B1 | 1/2001 | Nagle et al. |

OTHER PUBLICATIONS

Kwon, et al., "Electrically Erodible Polymer Gel for Controlled Release of Drugs," *Nature* 354:291–293 (1991).

Low, et al., "Microactuators Towards Microvalves for Responsive Controlled Drug Delivery," *Sensors & Actuators B* 67: 149–60 (2000).

Madou & Florkey, "From Batch to Continuous Manufacturing of Microbiomedical Devices," *Chem. Rev.*, 100:2679–92 (2000).

Madou, *Fundamentals of Microfabrication*, pp. 468–512 (CRC Press 1997).

Madou & He, "Exploitation of a Novel Artificial Muscle for Controlled Drug Delivery," pp. 495–497 (1999).

Surbled, et al., "Characterization of Sputtered TiNi Shape Memory Alloy Thin Films," *Jpn. J. Appl. Phys.* 38: L1547–L1549 (1999).

Surbled, et al., "Shape Memory Alloys for Micromembranes Actuation," *SPIE*. 3825: 63–70 (1999).

Surbled, et al., "Array of Shape Memory Alloy One–Shot Micro–Valves for Drug Delivery," MME '99, Gif sur Yvette, France (Sep. 27–28, 1999).

Tierney, et al., "New Electrorelease Systems Based on Microporous Membranes," *J. Electrochem. Soc.*, 137:3789–3793 (1990).

Tierney, et al., "Electroreleasing Composite Membranes for Delivery of Insulin and Other Biomacromolecules," *J. Electrochem. Soc.*, 137:2005–2006 (1990).

Uhrich, et al., "Synthesis and Characterization of Degradable Poly(anhydride–co–imides)," *Macromolecules* 28:2184–2193 (1995).

U.S. patent application Ser. No. 09/727,858, Richards et al., filed Dec. 1, 2000.

U.S. patent application Ser. No. 09/665,303, Santini et al., filed Sep. 19, 2000.

Vladimirsky, et al., "Thin Metal Film Thermal Micro–Sensors," *Proc. SPIE–Int. Soc. Opt. Eng.* 2640:184–92 (1995).

Wogersien et al., "Fabrication of Thin Film Resistors and Silicon Microstructures Using a Frequency Doubled Nd:YAG–Laser," *Proc. SPIE–Int. Soc. Opt. Eng.* 3680:1105–12 (1999).

METHODS AND DEVICES FOR SEALING MICROCHIP RESERVOIR DEVICES

CROSS-REFERENCE TO RELATED APPLICATIONS

Priority is claimed under 35 U.S.C. § 119 to U.S. provisional application Serial No. 60/207,814, filed May 30, 2000.

STATEMENT REGARDING FEDERALLY SPONSORED RESEARCH OR DEVELOPMENT

This invention was made with government support under NIH-1R24-AI47739 awarded by the National Institutes of Health. The government has certain rights in the invention.

BACKGROUND OF THE INVENTION

This invention relates to miniaturized devices for the controlled exposure or release of molecules such as drugs and/or secondary devices such as sensors.

U.S. Pat. No. 5,797,898 to Santini, et al. describes active or passive microchips for the delivery, i.e. release, of molecules such as drugs. These microchip devices contain reservoirs filled with the molecules to be released. In some embodiments, the reservoir openings must be sealed, after they are filled, to prevent leakage from or between any of the reservoirs. The '898 patent discloses that the reservoirs can be sealed, for example, with a waterproof epoxy or other material impervious to any fluids surrounding the device. It is important to avoid contacting the drug or other reservoir contents with the chemical adhesive. The use of such chemical adhesives may necessitate additional testing to determine the presence and nature of any interactions between the chemical adhesive and each drug or other chemical to be released. Furthermore, chemical adhesives may require long times, high temperatures, and/or exposure to ultraviolet light in order to cure completely. These curing processes, however, may degrade sensitive chemicals or drugs in the reservoir. It therefore would be advantageous to provide additional methods of sealing the device which do not require the use of chemical adhesives, or if used prevent contact between the adhesives and reservoir contents.

It is therefore an object of the present invention to provide devices and methods for sealing the reservoirs of microchip devices for the controlled release of drugs and other molecules, which do not require the use of chemical adhesives or sealants, or which prevent contact between the reservoir contents and the adhesives.

These and other objects, features, and advantages of the present invention will become apparent upon review of the following detailed description of the invention taken in conjunction with the drawings and the appended claims.

SUMMARY OF THE INVENTION

Methods and devices are provided for sealing the reservoirs of microchip devices to prevent leakage from or between any of the reservoirs. The methods advantageously prevent contact between the reservoir contents (e.g., molecules such as drugs and reagents or smaller devices such as sensing components) and chemical adhesives, if any, used in the sealing process. In a preferred embodiment, the sealing method comprises (i) providing a microchip device having a front side and a back side, wherein the back side has a plurality of reservoir openings in need of sealing; (ii) positioning a gasket material, such as a flexible polymeric sheet, over the reservoir openings; and (iii) securing one or more backplates over the gasket material to compress the gasket material to the back side of the microchip device so as to seal the reservoir openings. A barrier layer, such as polyethylene glycol, may be applied into/onto the reservoirs/substrate to provide a barrier between the reservoir contents and the sealing system.

Preferably, the backplate is secured by mechanical means; however, where a chemical adhesive is used in place or in conjunction with mechanical means, the gasket material is interposed between the reservoir openings and the chemical adhesive. In one embodiment, the mechanical means comprises securing the microchip device and the gasket material between a front sealing frame and the backplate. Mechanical securing means for attaching the backplate to the substrate of the microchip device or to the front sealing frame include the use of fasteners, crimping, pins/holes, soldering, and welding.

In another embodiment, the sealing method comprises (i) providing a microchip device having a front side and a back side, wherein the back side has a plurality of reservoir openings in need of sealing; and (ii) securing one or more composite backplates to the backside of the microchip device. The composite backplate includes one or more sealing plugs which seal the reservoir openings. The composite backplates also preferably are secured by mechanical means, although a chemical adhesive can be used where the sealing plugs are interposed between the reservoir openings and the chemical adhesive. In one embodiment, the composite backplate comprises a rigid substrate having a plurality of sealing plugs extending therefrom, such that the sealing plugs are aligned with and project, at least partially, into the reservoir openings. The sealing plugs can comprise a plurality of wells, which can contain the molecules or devices for introduction into the reservoirs of the microchip during the securing of the composite backplates.

The microchip devices sealed with these methods typically include reservoir caps useful in the controlled release and exposure of the molecules and devices contained therein. The methods include the steps of providing the microchip device at a site where the molecules or devices are to be delivered, and then controlling the release or exposure of the molecules or devices from the reservoir by diffusion through or disintegration of the reservoir cap.

DETAILED DESCRIPTION OF THE INVENTION

Methods have been developed to mechanically seal the reservoirs of microchip devices, such that chemical adhesives are not required, or if a chemical adhesive is used, it cannot contact the reservoir contents. The reservoirs must be sealed after the selected contents (e.g., molecules and/or devices) are introduced therein, so that the contents are stored and protected from the environment for a period of time until exposure to the environment is desired. The exposed molecule can be released from the reservoir or remain immobilized therein. The microchip devices provide selective and controlled exposure and/or release of the reservoir contents.

Microchip devices that can be mechanically sealed are described, for example, in U.S. Pat. Nos. 5,797,898 and 6,123,861, both to Santini, et al., which are incorporated by reference herein. A "microchip", as used herein, is defined as a miniaturized device fabricated using forming methods such as compression molding, injection molding, thermoforming, or other methods described in, for example, Tadmor & Gogos, *Principles of Polymer Processing*, (John Wiley & Sons, New York 1979), microinjection, microcontact printing, laser or ultrasound machining, and standard microelectronics processing methods such as photolithography, etching, evaporation, and sputtering as described, for example, in Wolf & Tauber, *Silicon Processing for the VLSI Era, Volume I—Process Technology* (Lattice Press, Sunset Beach, Calif. 1986); Jaeger, *Introduction to Microelectronic Fabrication, Volume V* in *The Modular Series on Solid State Devices* (Addison-Wesley, Reading, Mass. 1988); and Campbell, *The Science and Engineering of Microelectronic Fabrication* (Oxford University Press, New York 1996). The fabrication methods may be used to fabricate devices having primary dimensions (length of a side for square or rectangular devices, or diameter for round devices) that are typically a few centimeters, and preferably a few millimeters, or smaller. Device dimensions may vary depending on the application. The number and volume of the reservoirs will vary with the device dimensions. Devices for in vivo applications are small enough to be implanted, injected, orally administered, or attached to various mucous membranes.

Device Components and Materials

Each microchip device includes a substrate having a plurality of reservoirs (as described, for example, in U.S. Pat. No. 5,797,898 to Santini, et al.), and contents contained in the reservoir. The reservoir contents can be a chemical (e.g., a drug for release or a reagent or catalyst immobilized in the reservoir) and/or smaller devices or device components (e.g., a sensor). The reservoirs may include a release system. Each reservoir may or may not have a reservoir cap, which controls the time of release or exposure and may control the release rate.

Substrate

The microchip devices may be composed of any suitable material that may be fabricated by known methods, such as described in U.S. Pat. No. 6,123,861. Suitable materials include polymers, metals, semiconductors, and ceramic materials. Representative examples of suitable polymers include polyolefins such as polyethylene; fluorinated polymers such as polytetrafluoroethylene; silicones (polysiloxanes); and biodegradable polymers such as polyanhydrides; polyphosphazenes; pseudo polyamino acids; and polyesters such as polylactides, polyglycolides, and polylactones, and copolymers thereof. An example of a suitable semiconductor material include silicon. Representative examples of ceramic materials include alumina (aluminum oxide), aluminum nitride, silicon dioxide, silicon nitride, and other various nitrides and oxides.

For in vivo applications, the substrate generally is formed of or coated with a biocompatible material. For in vitro applications, such as in medical diagnostics, the substrate can be constructed of biocompatible or non-biocompatible materials.

Reservoir Caps and Release Systems

The release system may be comprised solely of the chemicals to be released in pure form (solid, liquid, or gel), or it may be a combination (for example, a matrix) of the chemicals to be released and other materials that affect the release rate and time through their degradation, dissolution, swelling, or disintegration. A release system may also include a material that does not undergo any of the above processes, but affects the release rate of the chemicals as they diffuse through it.

For embodiments of the microchip device in which it is desired to release chemicals (also referred to herein as "molecules") over a short period of time, reservoir caps or release systems, such as matrices, may be fabricated from degrading, dissolving, swelling, or disintegrating materials including, but not limited to, poly(lactide-co-glycolide) copolymers containing a high glycolide content, copolymers of polylactones with fast degradation times, certain polyanhydrides, hydrogels, oligosaccharides, polysaccharides, and metal foils, layers, or thin films (gold films, for example). For applications in which a longer use time is desirable, reservoir caps and release systems may be fabricated from materials that take longer to swell, degrade, dissolve, or disintegrate. Examples include resorbable biological materials such as cholesterol, other lipids and fats, and lipid bilayers, polymers such as polycaprolactone or certain polyanhydrides, and PLGA copolymers with high lactic acid content. For structures in which the chemicals to be released must diffuse through the release system, reservoir cap and/or release system materials may remain intact or break down, for example, by degrading, dissolving, swelling, or disintegrating.

As used herein, the terms "disintegrate," "disintegration," and "disintegrating" in reference to reservoir caps include any mechanism of loss of structural integrity and thus loss of barrier to the environment outside of the reservoir, including, but not limited to, oxidation, mechanical rupture, degradation or dissolving, unless otherwise indicated.

In one embodiment, the device includes a reservoir cap or membrane that functions to allow diffusion of an aqueous solution into the reservoir at a selected rate. The aqueous solution can displace the molecules to be released, e.g., an osmotic effect, and/or can swell a release system containing a water-swellable material to cause the reservoir cap to rupture and release/expose the reservoir contents.

For the active device, reservoir caps can be fabricated from non-conducting materials such as the polymers described above or conducting polymers including, but not limited to, polyaniline or polypyrrole. Electrically erodible polymers such as complexes of polyethyloxazoline and poly(methacrylic acid) can be used as a component of a release system (Kwon, et al., *Nature*, 354:291-93 (1991)), or a reservoir cap. Conducting polymers such as polypyrrole can be mixed with a chemical and used to deliver the chemical via electrophoresis (Miller, *Mol. Cryst. Liq. Cryst.*, 160:297–301 (1988)). Electrodes, circuitry, and conducting membranes which cover the reservoirs can be fabricated from materials including, but not limited to, conducting polymers such as polyaniline or polypyrrole, and metals such as copper, gold, and silver. Non-conducting, responsive reservoir membranes can be made from materials such as polymers that are sensitive to pH, electric field, or other environmental conditions.

In some embodiments, the release system should respond to the application of an electric current by either degrading or exchanging ions from solution with an active agent that is ionically bound to the polymer. Examples of materials for such release systems include copolymers of polyethyloxazoline and poly(methacrylic acid), which have been shown to degrade with an applied current. Other examples include release of edrophonium chloride (a positively charged molecule) through an ion-exchange mechanism using a copolymer of 2-acrylamido-2-methyl-1-propane sulfonic acid and n-butylmethacrylate, or release of dopamine from a composite polymer of poly(N-methylpyrrole) poly (strenesulfonate), upon application of an applied current.

Molecules and Devices to be Released/Exposed

The chemicals to be released from the microchip devices may be in pure solid, liquid, or gel form, or mixed with other materials that affect the release rate and/or time, by forming a phase or by providing a diffusional barrier, for example. Chemicals may be in the form of solid mixtures including, but not limited to, amorphous and crystalline mixed powders, monolithic solid mixtures, lyophilized powders, and solid interpenetrating networks; in the form of liquid mixtures including, but not limited to, solutions, emulsions, colloidal suspensions, and slurries; and in the form of gel mixtures including, but not limited to, hydrogels.

For in vivo applications, the chemical preferably is a therapeutic, prophylactic, or diagnostic agent. Examples include chemotherapeutic agents, hormones, and painkillers. An example of a diagnostic agent is an imaging agent such as a contrast agent. Other molecules that can be released include fragrances and flavoring agents.

In other embodiments, the reservoirs contain molecules such as catalysts and reagents and/or secondary devices such as sensors and sensing components. Examples of sensing components include components utilized in measuring or analyzing the presence, absence, or change in a chemical or ionic species, energy (or light), or one or more physical properties (e.g., pH, pressure) at a site. Proper functioning of certain reservoir contents, such as a catalyst or sensor, in these embodiments generally does not require their release from the reservoir; rather their intended function, e.g., catalysis or sensing, occurs upon exposure of the reservoir contents to the environment outside of the reservoir after opening of the reservoir cap, wherein the catalyst molecules or sensing component remain immobilized within the open reservoir.

Backplate Seal

After the reservoirs of the microchip device are filled, they are sealed by securing one or more backplates over the reservoir openings of the microchip device. The securing preferably is solely by mechanical means, as described herein. If a chemical adhesive is used to supplement or replace the mechanical means, then a gasket material or sealing plug (i.e. a separation device) is interposed between the reservoir contents and the chemical adhesive.

As used herein, the term "backplate" includes the "back sealing plates," "backing plate," and "composite backplates" described below, unless otherwise indicated, such as where the context indicates that only one or the other is referenced.

Plate and Frame Seal—Separate Gasket

Figure 1:
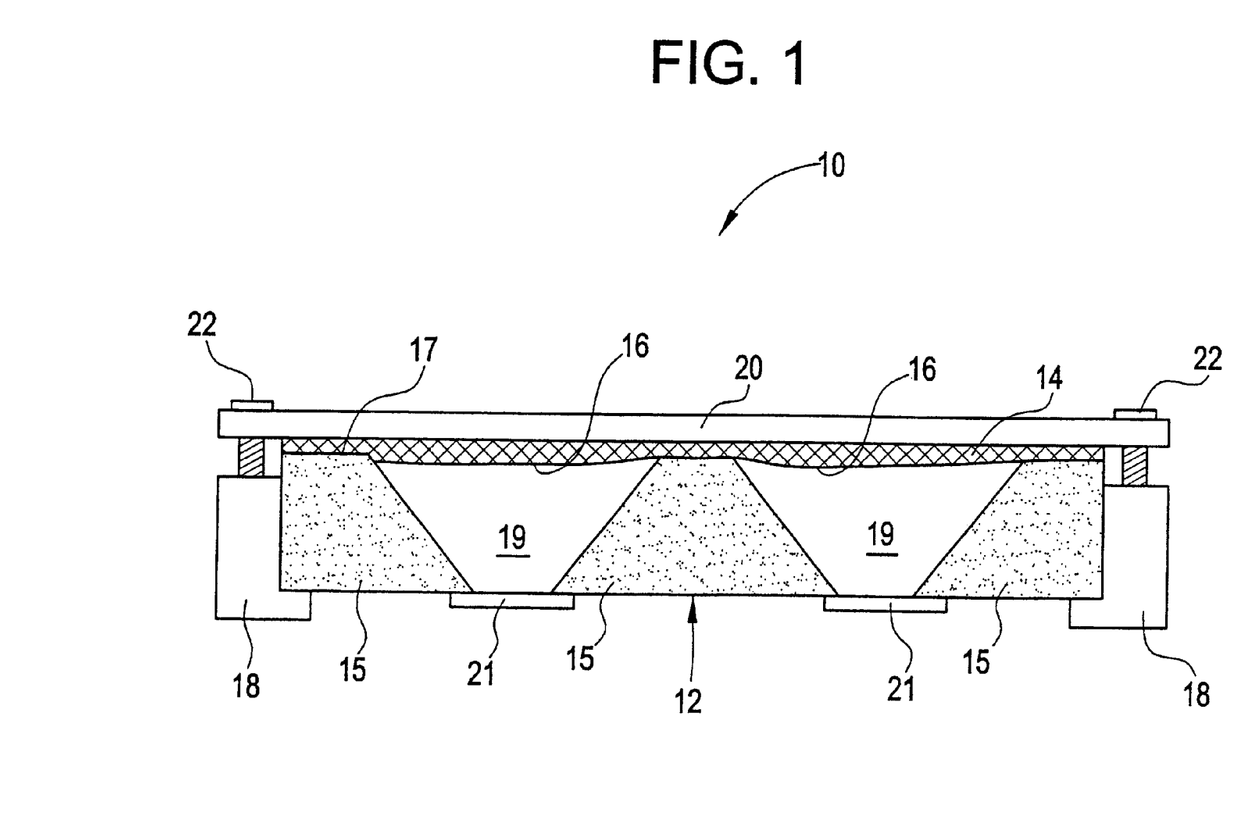
FIG. 1 is a cross-sectional view of a microchip device having reservoirs mechanically sealed using a gasket, a backing plate, and a frame.
Figure 2:
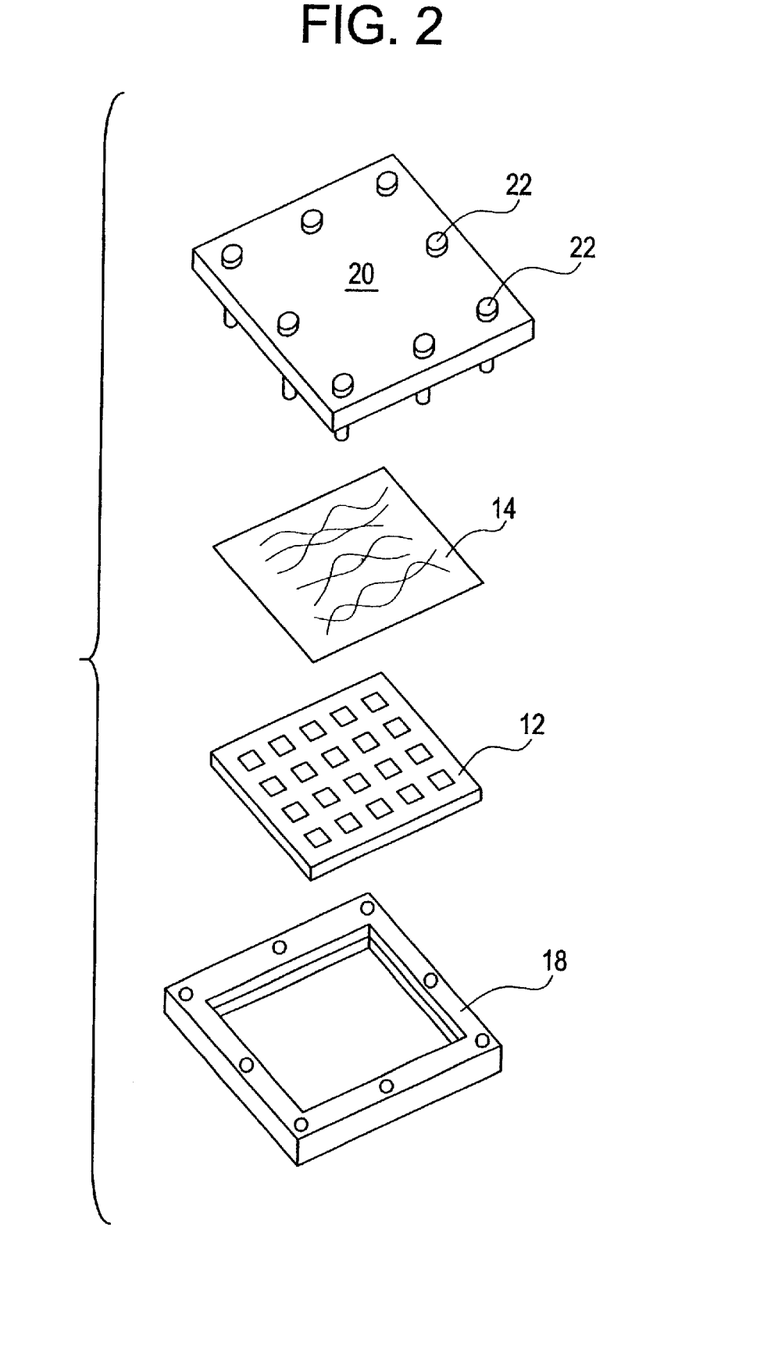
FIG. 2 is an exploded view of the components that may be assembled to mechanically seal the reservoirs of the microchip device shown in FIG. 1.

In a preferred embodiment, which is illustrated in FIGS. 1 and 2, the mechanically sealed microchip device 10 comprises a microchip device 12 and a gasket material 14 covering the reservoir openings 16 between a front sealing frame 18 and a back sealing plate 20, such that the gasket material 14 is compressed against the back side 17 of the microchip device 12 by the back sealing plate 20. Microchip device 12 includes substrate 15 having filled reservoirs 19, and reservoir caps 21. The front sealing frame 18 is secured to the back sealing plate 20 with screws 22. Other means of securing front sealing frame 18 to back sealing plate 20 can be used, including other fasteners, such as bolts/nuts, rivets, and spring clips; pins/holes; bending tabs; crimping; welding techniques, such as laser, ultrasonic, and solvent welding; soldering/brazing, and chemical adhesives (e.g., epoxy) isolated from the reservoir openings.

The front sealing frame and the back sealing plate generally are formed of a material that is more rigid than the chip matrix material. In one embodiment, the front sealing frame and the back sealing plate are formed of a biocompatible metal or rigid polymer. For in vivo applications, the material should be biocompatible and typically should resist degradation when contacted with biological fluids at the site of delivery, for at least the time required to complete delivery of the molecules. Examples of suitable materials include glasses; metals, such as stainless steel and titanium; and polymers, such as polyethylene, polytetrafluoroethylene and other fluorinated polymers, silicones (polysiloxanes), polyanhydrides, polyphosphazenes, polyhydroxyalkanoates, pseudo polyamino acids, and polyesters, such as polylactide, polyglycolide, and polylactones, and copolymers thereof. The front sealing frame and back sealing plate can be fabricated using methods known in the art, such as injection or compression molding, photolithography and etching, as well as machining or electro-machining.

The gasket material should be selected to provide appropriate mechanical properties (e.g., compressibility), biocompatibility, particularly for in vivo applications, impermeability, and compatibility with the reservoir contents. The gasket material preferably is in the form of a flexible sheet.

The gasket material preferably comprises one or more polymers, and can be in the form of a flexible polymeric sheet. As used herein, the term "polymer" in reference to gasket materials includes natural and synthetic elastomers and other polymers and cross-linked materials. Representative examples include collagen, chitosan, natural and synthetic rubbers, silicones, polyurethanes, and fluorinated polymers such as polytetrafluoroethylene. Elastomeric materials are preferred. Preferably, the gasket material is manufactured from a polymer that has been fully cured, with no residual plasticizer that could otherwise leach into the drug or into tissue surrounding the microchip device used in vivo applications.

The gasket material also may be chosen to limit diffusion of water vapor and other gases, for example to maximize the stability of certain drugs stored in the reservoirs. Silicone, for example, is particularly permeable to water and gases, whereas butyl rubber, neoprene, and fluoropolymer (e.g., VITON™) generally provide greater gas barrier properties.

The gasket material can be a composite. For example, the gasket material can be a mixture or layers of different materials. These different materials may be cross-linked to one another to varying degrees. In one embodiment, the gasket material comprises a polymer having a filler material (e.g., particulate or fibrous materials) dispersed throughout. In another embodiment, the gasket material has a laminate structure. The materials and structure of the gasket material can be varied to achieve particular properties such as biocompatibility, compatibility with the reservoir contents (e.g., the drug), modulus (durometer), and dimensional/chemical stability.

In some embodiments, it may be beneficial to use a multi-layered gasket material. For example, a bi-layer gasket could be used that consists of a first layer of a thin, smooth, hard elastomer for contacting the back of the microchip device over the reservoir openings, and a second layer of a softer elastomer for contacting the backing plate, where the softer layer aids in distributing the securing compression from the backing plate more evenly across the microchip device. Other examples of means for equalizing the securing compression include the use of a foam rubber layer behind the hard elastomer layer or the use of a bladder containing a compressible material behind the hard elastomer layer. Such evenness of securing compression may be important, particularly for larger sized microchips, in assuring sealing of all reservoir openings.

Variations of the frame and plate sealing mechanism are illustrated in FIGS. 3–7. These Figures include exploded views of the frame and plate components. The gasket material, which would be present, is not shown in FIGS. 3–5.

Figure 3A:
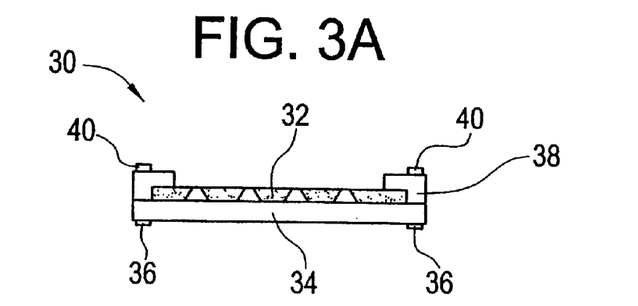
FIG. 3A is a cross-sectional view of a microchip device sealed with one embodiment of a plate and frame mechanical seal.
Figure 3B:
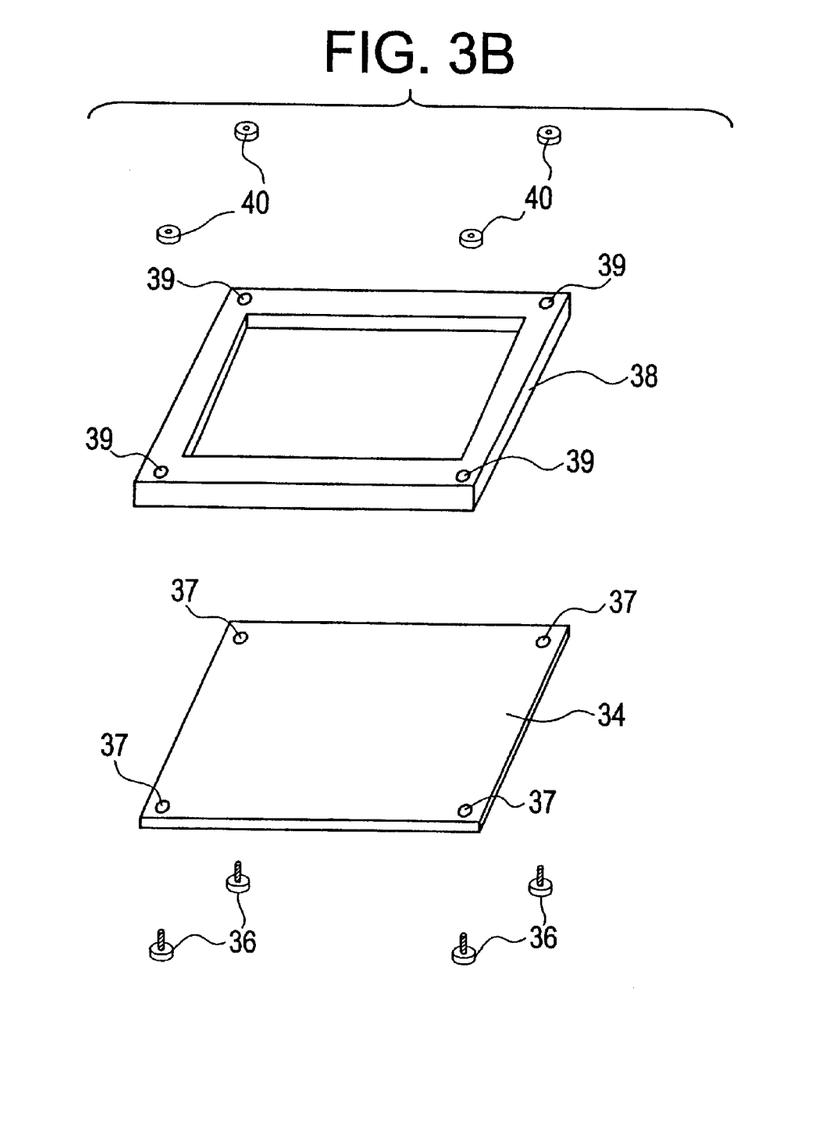
FIG. 3B is an exploded view of the sealing components of the plate and frame mechanical seal in FIG. 3A.

FIG. 3A shows, in cross-section, an embodiment similar to that described and shown in FIG. 1. The device 30 includes a microchip 32 mechanically sealed with backing plate 34 and sealing frame 38, which are secured together with bolts 36 and nuts 40. FIG. 3B is an exploded view of the sealing components, showing backing plate 34 and sealing frame 38 having apertures 37 and 39, respectively, through which bolts 36 connect to nuts 40.

Figure 4A:
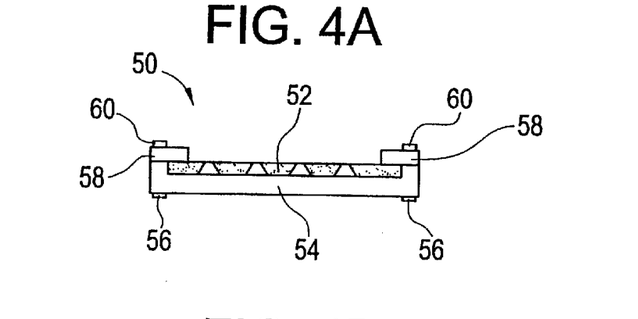
FIG. 4A is a cross-sectional view of a microchip device sealed with a second embodiment of a plate and frame mechanical seal.
Figure 4B:
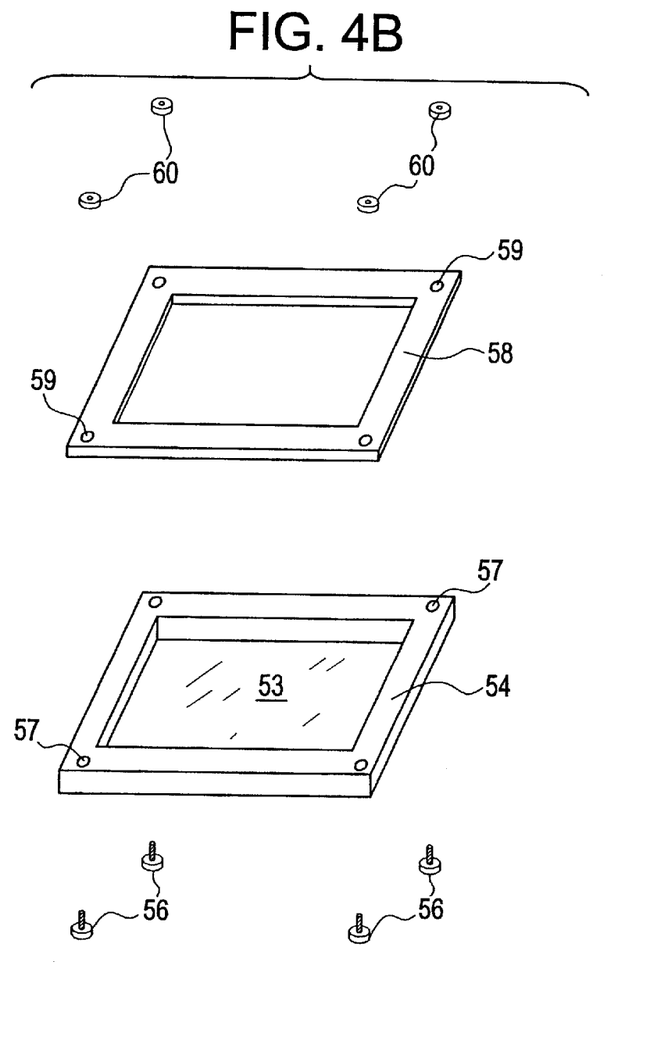
FIG. 4B is an exploded view of the sealing components of the plate and frame mechanical seal in FIG. 4A.

FIG. 4A shows another embodiment, in cross-section. The device 50 includes microchip 52 mechanically sealed with backing plate 54 and sealing frame 58, which are secured together with bolts 56 and nuts 60. FIG. 4B is an exploded view of the sealing components, showing backing plate 54 and sealing frame 58 having apertures 57 and 59, respectively, through which bolts 56 connect to nuts 60. In this embodiment, the back sealing plate 30 has an indentation 53 to receive the microchip 12.

Figure 5A:
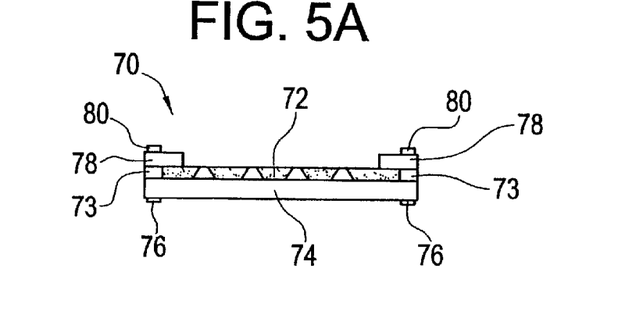
FIG. 5A is a cross-sectional view of a microchip device sealed with a third embodiment of a plate and frame mechanical seal.
Figure 5B:
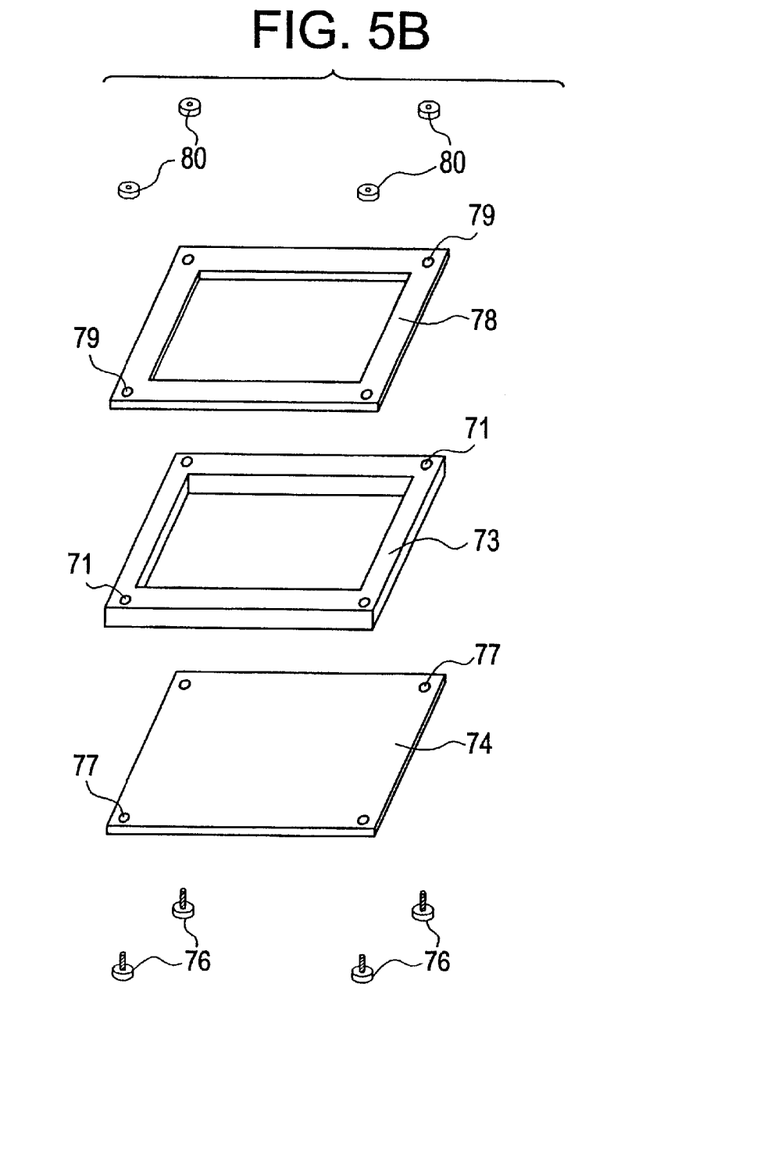
FIG. 5B is an exploded view of the sealing components of the plate and frame mechanical seal in FIG. 5A.

FIG. 5A shows another embodiment, in cross-section. The device 70 includes three separate plate/frame components: a backing plate 74 which is flat, a middle frame 73 having a cutout that surrounds microchip 72, and a front sealing frame 78 to secure the microchip 12 against the backing plate 74. The components are secured together with bolts 76 and nuts 80. FIG. 5B is an exploded view of the sealing components, showing backing plate 74, middle frame 73, and sealing frame 78 having apertures 77, 71, and 79, respectively, through which bolts 76 connect to nuts 80.

As described above, the securing compression typically is evenly applied across the gasket material and microchip device to maximize seal performance. Seal performance also may be enhanced by limiting the magnitude of the securing compression, for example at a particular strain level. This limiting may be achieved with the use of a positive compression stop. For example, compare the device of FIG. 1 which does not have a positive compression stop and the devices of FIGS. 3–5 include a positive compression stop. The desired securing compression may be specified in terms of force or displacement (i.e. strain), depending, for example, on the type and thickness of the particular gasket material, and whether a positive compression stop is provided in the particular plate/frame design. For example, if the thickness of the gasket material varies significantly across the sheet, then it may be preferable to apply a particular force rather than a particular displacement. The specification of any one of these factors may impact the selection of another. In one alternative embodiment, adequate sealing can be quantified by measuring the amount of torque applied to bolts used to secure the gasket material. This torque may or may not directly correlate with either strain or compressive force, but can nonetheless provide a means for assuring a consistent, effective seal.

One generally may follow the sealing recommendations provided by the manufacturer of a particular elastomeric sheet or other gasket material. It is estimated that strains between about 5 and 20% provide an effective seal for many elastomeric gasket materials. Too much strain can cause the substrate of the microchip device to fracture. The degree of compression will depend on several factors, including the durometer hardness of the gasket material, the thickness of the gasket material, and the surface roughness of the gasket material. In one embodiment, for example, a silicone rubber sheet having a durometer hardness of 40 on the shore A scale and a thickness of 0.065 inches (1.65 mm) is compressed by 0.0035 inches (0.089 mm) to effect sealing.

The selection of the embodiment will depend, in part, on the relative ease and costs of manufacturing and assembling the different parts. In one embodiment, the apertures in the sealing plate and/or backing frame can be threaded, such that the use of the nuts is no longer required to secure a screw or bolt through the plate and frame components.

Figure 6A:
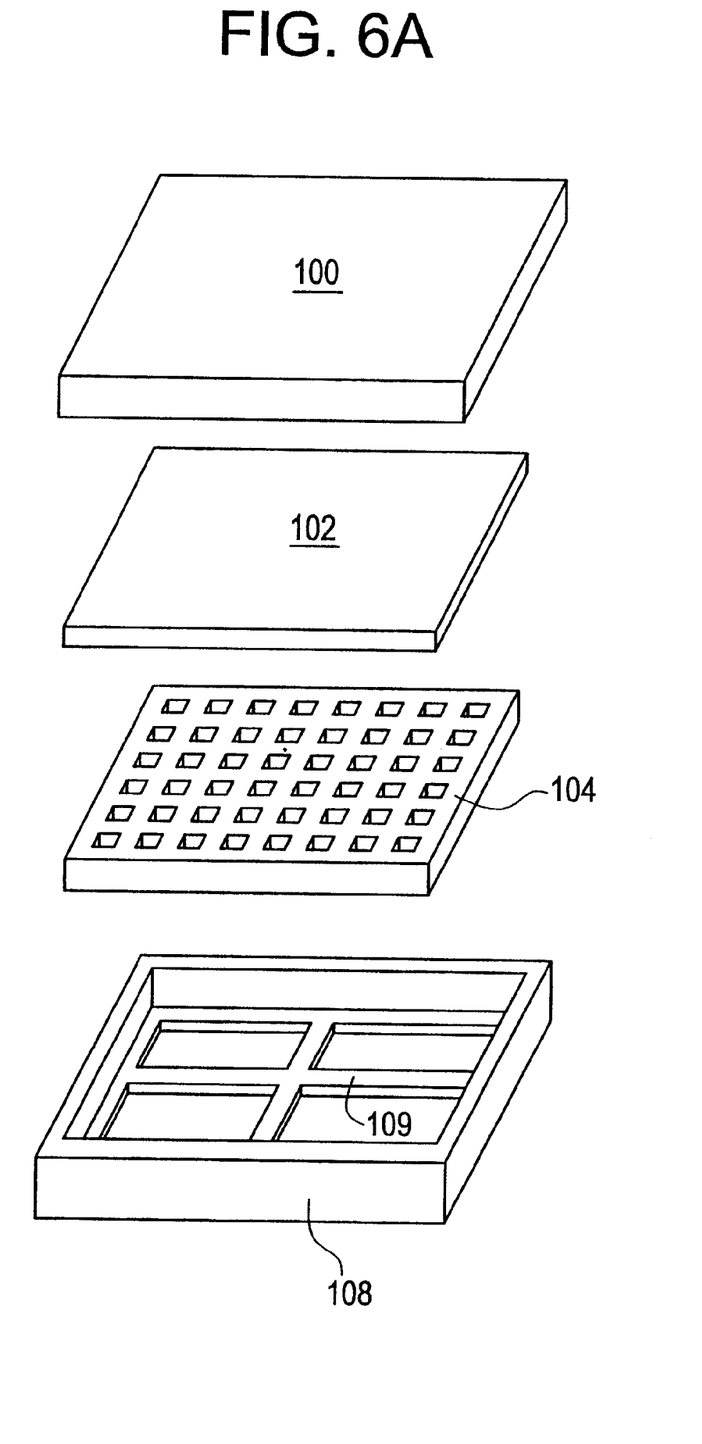
FIG. 6A is an exploded view of one embodiment of a microchip device and mechanical sealing components wherein the sealing frame includes cross-braces.
Figure 6B:
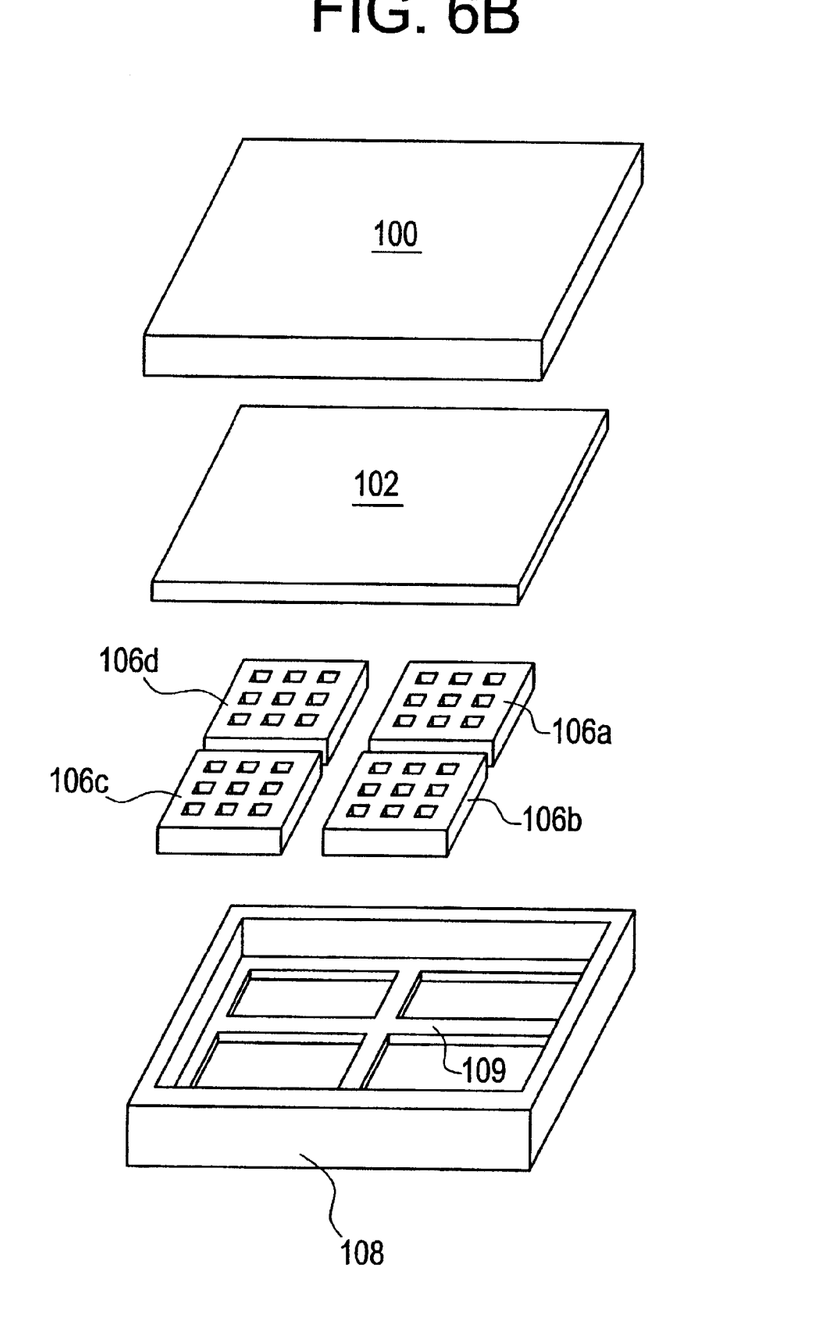
FIG. 6B is an exploded view of another embodiment wherein the sealing frame includes cross-braces and a single plate and frame seals an array of four microchips.

As illustrated in FIGS. 6A and 6B, the front sealing frame may contain one or more cross-braces over the front of the chip to provide mechanical support to prevent deflection of the microchip if the elastic deflection of the microchip is too large or to otherwise mechanically support and protect the microchip. In FIG. 6A, shown in an exploded view, backing plate 100 covers gasket material 102 which seals the reservoir openings of microchip 104 in from sealing frame 108, which has cross-braces 109. The device of FIG. 6B is identical to that of FIG. 6A except that microchip 104 has been replaced with an array of four microchips 106a, 106b, 106c, and 106d. The cross-braces advantageously permit an array of two or more microchips to be sealed within a single frame. Preferably, the cross-braces contact the microchips along their joints (i.e. interfaces) with one another so as to prevent the microchips from slipping out of the sealing frame, while avoiding blocking any reservoir caps.

Figure 8A:
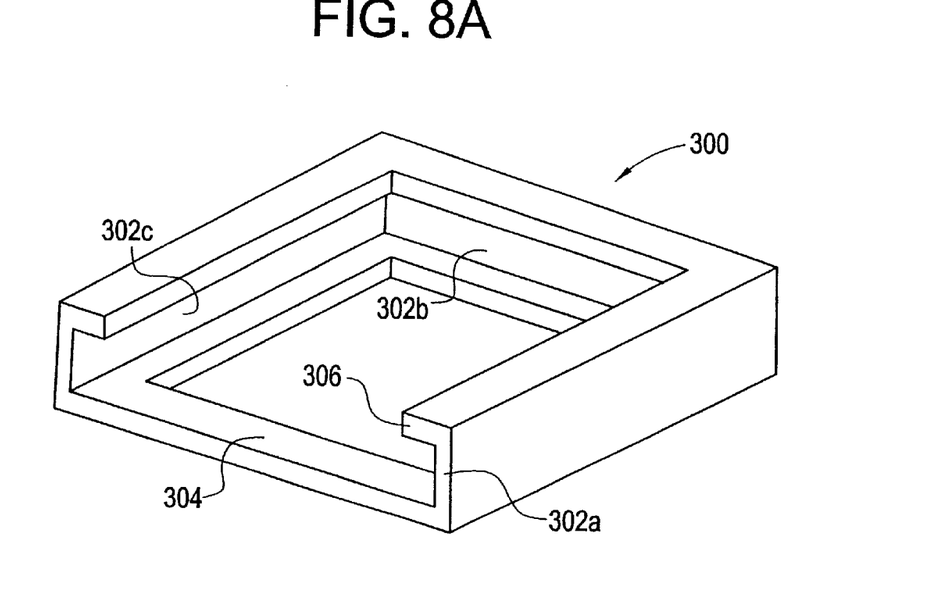
FIGS. 8A and 8B are perspective views of a slotted frame without and with a microchip device secured within the frame, respectively.
Figure 8B:
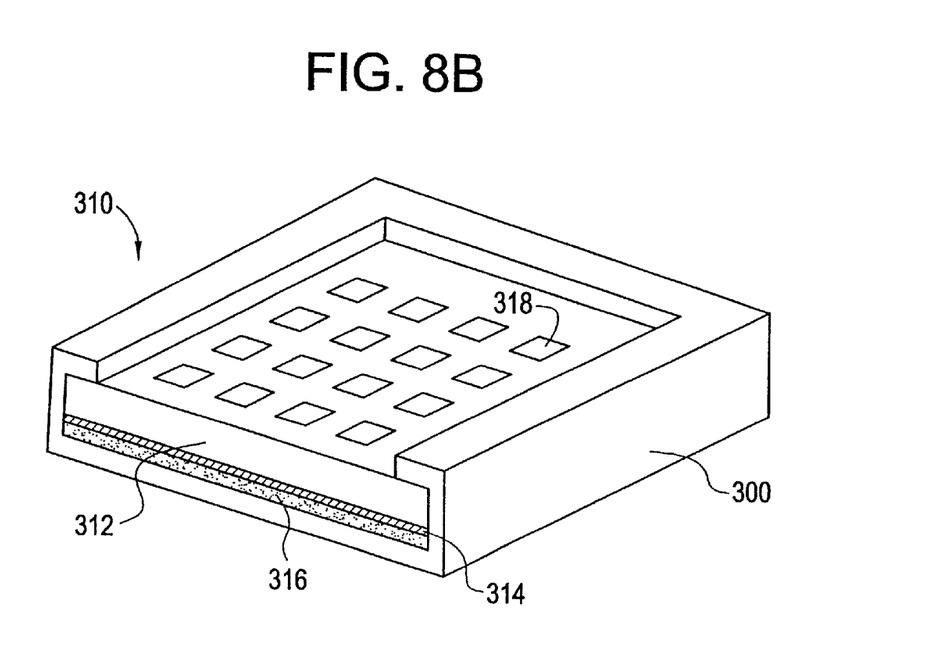

In another embodiment, a slotted frame can be used. An example is illustrated in FIGS. 8A and 8B. FIG. 8A shows a slotted frame 300 having a slot defined by sidewalls 302a, 302b, and 302c, back frame 304, and top lip 306. FIG. 8B shows an assembled device 310 formed of the slotted frame 300 into which a microchip device 312, a gasket material 314, and a backing plate 316 have been slid into the slot of slotted frame 300. These components are dimensioned such that in the assembled position, the backing plate 316 exerts a securing compression on the gasket 314 and back side of the microchip device 312 over the reservoir openings (hidden in the Figure). Reservoir caps 318 are shown on the top side of the microchip device 312 in FIG. 8B.

Backplate Without Frame

In another embodiment, the backplate can be secured over the reservoir openings without the use of a front frame, by directly attaching the backplate to the microchip device. This attachment can be accomplished by a variety of techniques, including mechanical and chemical means. For example, a chemical adhesive can be used between the backplate and microchip device at a position beyond the periphery of the gasket material, such that the gasket material is interposed between the reservoir contents and the chemical adhesive. Alternatively or additionally, the backplate and microchip device can be mechanically attached. For example, these two components can be attached by fastener means, such as screws or rivets, or by providing the backplate and the microchip device with a plurality of holes and corresponding pins along the periphery of these two components, such that the holes and pins can be aligned and frictionally engaged to secure the backplate and microchip device together. As another example, one or both of these two components could be provided with a plurality of folding tabs along their peripheries, such that a tab on the edge of the microchip device, for example, can be folded or bent around to the distal surface of the backplate when the proximal surface of the backplate is positioned adjacent and over the reservoir openings of the microchip device, with a gasket material or sealing plug appropriately interposed.

In one embodiment, the outer periphery of the backside of microchip device (reservoir opening side) is provided with a metal coating (for example by deposition) and the proximal surface of the backplate comprises metal. The backplate can either be formed of metal or it can be a non-metal having a metal coating. The two metal surfaces are then fused together, for example by soldering or welding.

Composite Backplate

In alternative embodiments, a composite backplate can be used in place of the separate compliant gasket and rigid backplate, to mechanically seal the reservoirs. For example, the composite backplate can be a laminated structure having a rigid layer to provide the structural support required to function with the frame, and a soft or flexible layer to provide the sealing function.

Figure 7:
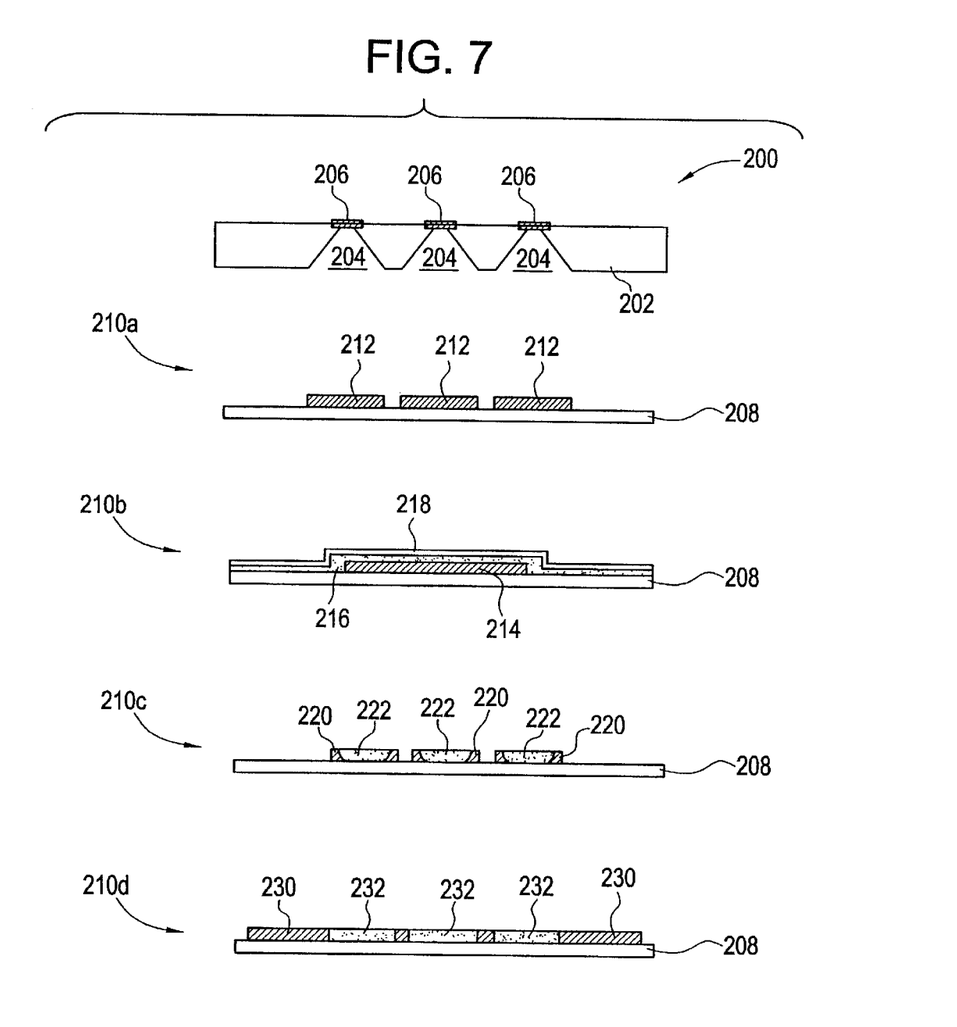
FIG. 7 is a cross-sectional view of a microchip device and four embodiments of composite backplates that can be used to seal the reservoirs of the microchip device.

Other representative examples of the composite backplate are shown in FIG. 7 with microchip 200 having substrate 202 containing reservoirs 204 covered by reservoir caps 206. FIG. 7 further includes four variations of composite backplates, 210a, 210b, 210c, and 210d, which can be mated with microchip 200 to seal, and optionally to fill, the reservoirs 204.

The composite backplate 210a includes a solid substrate 208 on which sealing plugs 212 are defined, for example by using a photolithographic process, soft lithography, contact printing, or screen printing. The sealing plugs can be made, for example, from a photocrosslinked silicone rubber. This approach may simplify sealing of the devices. For example, the sealing process could include (i) loading a drug into reservoirs 204; (ii) aligning and pressing composite backplate 210a against microchip substrate 202 with force sufficient to seal reservoirs 204 with sealing plugs 212, yet leaving a gap between substrate 208 and microchip substrate 202; and then (iii) wicking (e.g., by using capillary forces) an adhesive material such as epoxy into the gap and curing to bond composite backplate 210a and microchip 200 together. If needed, the surfaces of the chip and backplate can be treated or modified to improve adhesion. The silicone plugs act to seal the reservoirs (i.e. wells) and protect the drug from the adhesive.

The composite backplate also can be mechanically secured to seal the reservoirs, for example, using mechanical techniques described above when using separate gasket materials. These mechanical means can supplement or replace the use of an adhesive material.

The composite backplate 210b includes a solid substrate 208 on which a sealing plug 214 is defined, a metal layer 216 deposited (e.g., by evaporation) over the sealing plug 214, and a polymer layer 218 coated onto the metal layer 216. The metal layer 216, such as aluminum, provides improved barrier properties to the sealing plug (e.g., reducing gas transmission through it). The polymer layer 218 should be soft and flexible enough to improve the sealing function of the sealing plug 214. The polymer layer 218 also can prevent contact of the metal with the contents in the reservoir 204.

The sealing plugs and gasket material can be fabricated with wells, which then can be filled with drug. This may be useful, for example, if the filling process may damage the microchips, by putting too much stress on a gold membrane reservoir cap. Furthermore, filling (and validation of same) may be easier using the backplate, particularly if the substrate is transparent.

Composite backplates 210c and 210d are representative of embodiments in which drug is loaded into the backplate/gasket material, rather than into reservoirs 204. The composite backplates 210c and 210d hold the drug, thereby combining the assembly step of filling the reservoirs and sealing them. Composite backplate 210c includes substrate 208 on which sealing plugs 220 are defined. The sealing plugs 220 include wells filled with drug 222. Composite backplate 210d includes substrate 208 onto which gasket material 230 is attached or formed. The gasket material 230 includes wells filled with drug 232.

Liquid-Applied Barrier Layer

In another embodiment, a barrier material is applied into the reservoirs over the reservoir contents and, typically, the surface the substrate adjacent the reservoir openings. The barrier material is applied in liquid form and solidifies or gels to form a substantially non-porous (solid or gel) barrier layer. The barrier layer must be compatible with the reservoir contents, and must provides a barrier between the contents of the reservoir, e.g., drug molecules, and any chemical adhesives that may be used in sealing or coating the device.

In a preferred embodiment, the barrier material is polyethylene glycol (PEG), which is a non-ionic, water soluble polymer, available in a wide range of molecular weights. PEG is a preferred material since it has previously been well characterized in many clinical studies. PEGs having molecular weights greater than 1000 g/mol are solids at temperatures less than about 40 to 50° C. and are preferred. Such a PEG can be readily heated and liquefied for application to the substrate/reservoirs in a molten phase. Upon contact with the colder substrate/reservoir contents, the PEG will solidify. Higher molecular weight PEGs can be used with aqueous or non-aqueous polar solvents to form a solution for application to the substrate/reservoirs. A wide range of solvent chemistry is available, providing control over the evaporation rate and therefore the rate of solidification of the PEG, so that the degree of mixing at the interface with the reservoir contents can be limited. Application can be, for example, by microinjection or ink jet printing techniques.

Following deposition of the barrier layer, any type of mechanical or chemical sealing system can be applied over or onto the solid PEG surface. When a chemical sealing system is employed (e.g., epoxy), little or no mixing should occur at the interface prior to cross-linking the sealing system, primarily because PEG is polar and many curable sealing systems are non-polar in nature.

Methods of Fabricating and Assembling the Sealed Devices

The basic microchip devices (i.e. substrate, reservoirs, reservoir caps, and release system) can be made using microfabrication methods known in the art, particularly those methods described in U.S. Pat. Nos. 5,797,898 and 6,123,861, both to Santini, et al., which are hereby incorporated by reference in their entirety, with the exception that, after the reservoirs are filled with the molecules to be released, the reservoir openings are not sealed chemically, that is, using an adhesives and/or epoxy coatings. Rather, the reservoir openings are sealed mechanically as described herein. The basic microchip devices can also be made using molding techniques, as known in the art or as described in U.S. application Ser. No. 09/727,858, filed Dec. 1, 2000, by Richards et al., which is incorporated herein by reference.

In a preferred embodiment, the method of the mechanical sealing comprises sandwiching the microchip device and a gasket material covering the reservoir openings between a front sealing frame and a back sealing plate, such that the gasket material is compressed against the back side of the microchip device by the back sealing plate. The front sealing frame is secured to the back sealing plate using fasteners, such as bolts, rivets, screws, or spring clips; hole/pins; bending tabs; or a welding technique, such as laser welding, ultrasonic welding, or solvent welding.

Another means for securing the gasket material to the back of the microchip device includes evacuating the dead spaces in the reservoirs (i.e. the space between the top of the reservoir contents and substrate surface at reservoir opening). This could be used in conjunction with another other means for attaching a backplate to the microchip device, with or without a frame.

Using the Microchip Devices

Operation/Release

Representative methods of release include degradation, dissolution, swelling, or disintegration of a release system containing the pure chemicals to be released, or a mixture of the chemicals and an excipient material that affects the release rate and/or time of the chemicals. Passive devices will not require the application of a stimuli source to effect these changes. Active devices may be controlled by microprocessors, remote control, or biosensors. Typical control methods include electric potential and pH control methods, whereby the application of a potential causes electrochemical reactions to occur which cause the direct dissolution, degradation, swelling, disintegration, or other change in the reservoir cap, membrane, or release system, or which change the pH in the local environment and thus effect a change in the materials of the reservoir caps or release systems which will cause the chemicals of interest to be released from the reservoir. Examples of release methods include, but are not limited to, simple dissolution of a reservoir membrane due to an electrochemical reaction, electrophoretic delivery of a chemical from a release system in a reservoir, release of a chemical from reservoir due to ion exchange, or swelling of a release system which causes the reservoir cap or membrane to rupture, thereby releasing a chemical from the reservoir.

Applications

Passive and active devices have numerous in vivo, in vitro, and commercial diagnostic applications. The microchips are capable of delivering precisely metered quantities of molecules and thus are useful for in vitro applications, such as analytical chemistry and medical diagnostics, as well as biological applications such as the delivery of factors to cell cultures. In other applications, the devices are used to control release of fragrances, dyes, or other useful chemicals.

In one embodiment, the microchip devices can be used in vivo for the delivery of drugs to humans and other animals. The microchips are especially useful for drug therapies in which it is desired to control the exact amount, rate, and/or time of delivery of the drug. Preferred drug delivery applications include the delivery of potent compounds such as hormones, chemotherapy medications, and some strong painkillers. The microchips can be implanted via surgical procedures or injection, or swallowed, and can deliver many different drugs, at varying rates and varying times.

Modifications and variations of the methods and devices described herein will be obvious to those skilled in the art from the foregoing detailed description. Such modifications and variations are intended to come within the scope of the appended claims.

We claim:

1. A microchip device for the release or exposure of molecules or devices, comprising:

a substrate having a front side, a back side, and at least two reservoirs which contain said molecules or devices, the reservoirs having reservoir openings on the back side of the substrate;

a reservoir cap positioned on the front side of the substrate on each reservoir over the molecules or devices, wherein release or exposure of the molecules or devices from the reservoir is controlled by diffusion through or disintegration of the reservoir cap;

a gasket material positioned over the reservoir openings; and one or more backplates secured over the gasket material to compress the gasket material to the back side of the microchip device to seal the reservoir openings.

2. The device of claim 1, wherein the one or more backplates are secured by mechanical means.

3. The device of claim 1, wherein the one or more backplates are secured with a chemical adhesive, and the gasket material is interposed between the reservoir openings and the chemical adhesive.

4. The device of claim 2, further comprising a front sealing frame secured to the backplate, wherein the substrate and the gasket material are secured between the front sealing frame and the backplate.

5. The device of claim 1, wherein the gasket material is a flexible polymeric sheet.

6. The device of claim 4, wherein the front sealing frame is attached to the back sealing plate with fasteners, crimping, pins/holes, soldering, or welding.

7. The device of claim 6, wherein the fasteners are selected from the group consisting of bolts, rivets, screws, bending tabs, and spring clips.

8. The device of claim 4, wherein the front sealing frame comprises a slotted frame having a slot into which the substrate, the gasket material, and the backplate are secured.

9. The device of claim 1, wherein a two or more substrates are secured between a front sealing frame and said one or more backplate.

10. The device of claim 1, further comprising a barrier layer interposed between the molecules or devices and the gasket material.

11. The device of claim 10, wherein the barrier layer comprises polyethylene glycol.

12. A microchip device for the release or exposure of molecules or devices, comprising:

a substrate having a front side, a back side, and at least two reservoirs which contain said molecules or devices, the reservoirs having reservoir openings on the back side of the substrate;

a reservoir cap positioned on the front side of the substrate on each reservoir over the molecules or devices, wherein release or exposure of the molecules or devices from the reservoir is controlled by diffusion through or disintegration of the reservoir cap;

one or more backplates secured to the back side of the microchip device; and a barrier layer positioned between the backplates and the molecules or devices, wherein the backplates and barrier layer cooperate to seal the reservoir openings.

13. A method for the release or exposure of molecules or devices, comprising:

providing at a site where the molecules or devices are to be delivered the microchip device of claim 1, and controlling the release or exposure of the molecules or devices from the reservoir by diffusion through or disintegration of the reservoir cap.

14. A method for sealing reservoirs containing molecules or devices in a microchip device, the method comprising:

providing a microchip device having a front side and a back side, wherein the back side has a plurality of reservoir openings in need of sealing;

positioning a gasket material over the reservoir openings; and securing one or more backplates over the gasket material to compress the gasket material to the back side of the microchip device so as to seal the reservoir openings.

15. The method of claim 14, wherein the one or more backplates are secured by mechanical means.

16. The method of claim 14, wherein a chemical adhesive is used to secure the one or more backplates, and the gasket material is interposed between the reservoir openings and the chemical adhesive.

17. The method of claim 15, wherein the mechanical means comprises securing the microchip device and the gasket material between a front sealing frame and the backplate.

18. The method of claim 14, wherein the gasket material is a flexible polymeric sheet.

19. The method of claim 17, wherein the front sealing frame is attached to the back sealing plate using fasteners, crimping, pins/holes, soldering, or welding.

20. The method of claim 19, wherein the fasteners are selected from the group consisting of bolts, rivets, screws, bending tabs, and spring clips.

21. The method of claim 19, wherein the welding is selected from the group consisting of laser welding, ultrasonic welding, and solvent welding.

22. The method of claim 17, wherein the front sealing frame comprises a slotted frame having a slot into which the microchip device, the gasket material, and the backplate are secured.

23. The method of claim 17, wherein a plurality of microchip devices are secured within a single front sealing frame.

24. The method of claim 14, further comprising applying a liquid barrier material into the reservoirs which solidifies to form a barrier layer interposed between the molecules or devices and the gasket material.

25. The method of claim 24, wherein the barrier layer comprises polyethylene glycol.

* * * * *